ns010376698B2

(12) United States Patent
Kulkarni et al.

(10) Patent No.: US 10,376,698 B2
(45) Date of Patent: Aug. 13, 2019

(54) SYSTEMS AND METHODS FOR GRADUALLY ADJUSTING A CONTROL PARAMETER ASSOCIATED WITH A COCHLEAR IMPLANT SYSTEM

(71) Applicant: ADVANCED BIONICS AG, Staefa (CH)

(72) Inventors: Abhijit Kulkarni, Newbury Park, CA (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 244 days.

(21) Appl. No.: 15/500,494

(22) PCT Filed: Aug. 14, 2014

(86) PCT No.: PCT/US2014/051087
§ 371 (c)(1),
(2) Date: Jan. 30, 2017

(87) PCT Pub. No.: WO2016/024978
PCT Pub. Date: Feb. 18, 2016

(65) Prior Publication Data
US 2017/0224992 A1    Aug. 10, 2017

(51) Int. Cl.
*A61N 1/36* (2006.01)
*A61N 1/372* (2006.01)
*H04R 25/00* (2006.01)

(52) U.S. Cl.
CPC ..... *A61N 1/36036* (2017.08); *A61N 1/37241* (2013.01); *A61N 1/37264* (2013.01); *H04R 25/70* (2013.01)

(58) Field of Classification Search
CPC ............ A61N 1/36039; A61N 1/36038; A61N 1/37241
See application file for complete search history.

(56) References Cited

U.S. PATENT DOCUMENTS 6,157,861 A    12/2000 Faltys et al.
6,355,064 B1    3/2002 Peeters et al.
(Continued)

FOREIGN PATENT DOCUMENTS

DE    19542961    5/1997
EP    2635046    9/2013
(Continued)

OTHER PUBLICATIONS

International Search Report and Written Opinion received in International Application No. PCT/US14/051087, dated Dec. 23, 2014.
(Continued)

*Primary Examiner* — George R Evanisko
(74) *Attorney, Agent, or Firm* — ALG Intellectual Property, LLC

(57) ABSTRACT

An exemplary sound processor included in a cochlear implant system associated with a patient 1) receives, from a fitting system while the sound processor is communicatively coupled to the fitting system, a command that sets a control parameter associated with the cochlear implant system to an initial value and data representative of a target value associated with the control parameter, 2) detects a decoupling of the sound processor from the fitting system, the decoupling resulting in the sound processor being in a non-fitting state, and 3) gradually adjusts, while the sound processor is in the non-fitting state, the control parameter from the initial value towards the target value in accordance with an adaption time course associated with the control parameter. Corresponding systems and methods are also disclosed.

17 Claims, 8 Drawing Sheets

(56) References Cited

U.S. PATENT DOCUMENTS

| | | |
|---|---|---|
| 7,961,898 B2 | 6/2011 | Van den Heuvel |
| 8,155,747 B2 | 4/2012 | Faltys et al. |
| 8,565,889 B2 | 10/2013 | Spitzer |
| 8,571,674 B2 | 10/2013 | Nicolai et al. |
| 8,644,535 B2 | 2/2014 | Steinbuss |
| 8,644,536 B2 | 2/2014 | Van den Heuvel |
| 9,179,231 B2 | 11/2015 | Johnston et al. |
| 2004/0047474 A1 | 3/2004 | Vries et al. |
| 2004/0190739 A1* | 9/2004 | Bachler ............ H04R 25/305 381/314 |
| 2005/0036637 A1 | 2/2005 | Janssen |
| 2005/0261748 A1 | 11/2005 | van Dijk |
| 2006/0089561 A1 | 4/2006 | Eder et al. |
| 2007/0043403 A1 | 2/2007 | Blamey et al. |
| 2007/0147624 A1 | 6/2007 | Fischer |
| 2007/0280494 A1 | 12/2007 | Hamacher |
| 2008/0107296 A1 | 5/2008 | Bachler et al. |
| 2008/0267434 A1 | 10/2008 | Schumaier |
| 2009/0264962 A1 | 10/2009 | Faltys et al. |
| 2010/0145411 A1 | 6/2010 | Spitzer |
| 2010/0161000 A1 | 6/2010 | Litvak et al. |
| 2010/0202625 A1 | 8/2010 | Boretzki et al. |
| 2010/0296679 A1 | 11/2010 | Hofmann et al. |
| 2011/0064241 A1 | 3/2011 | Kulkarni |
| 2011/0077698 A1 | 3/2011 | Tsampazis et al. |
| 2011/0642410 | 3/2011 | k |
| 2011/0106209 A1 | 5/2011 | Saoji |
| 2011/0235814 A1* | 9/2011 | Van Den Heuvel ... H04R 25/70 381/60 |
| 2011/0238176 A1 | 9/2011 | Bradley et al. |
| 2011/0249839 A1* | 10/2011 | Mindlin ............ H04R 25/43 381/314 |
| 2012/0109006 A1 | 5/2012 | James et al. |
| 2012/0219159 A1 | 8/2012 | Burk et al. |
| 2013/0114836 A1 | 5/2013 | Fichtl et al. |
| 2014/0086439 A1 | 3/2014 | Johnston et al. |
| 2014/0114375 A1 | 4/2014 | Chapa et al. |
| 2015/0335890 A1 | 11/2015 | Fredelake et al. |

FOREIGN PATENT DOCUMENTS

| | | |
|---|---|---|
| WO | WO-97/38653 | 10/1997 |
| WO | WO-2001/026419 | 4/2001 |
| WO | WO-2008/092183 | 8/2008 |
| WO | WO-2010/031880 | 3/2010 |
| WO | WO-2011/032021 | 3/2011 |
| WO | WO-2011/051831 | 5/2011 |
| WO | WO-2012/056427 | 5/2012 |
| WO | WO-2012/161717 | 11/2012 |
| WO | WO-2012/166108 | 12/2012 |
| WO | WO-2014/108201 | 7/2014 |
| WO | WO-2016/004970 | 1/2016 |
| WO | WO-2016/024978 | 2/2016 |

OTHER PUBLICATIONS

Non-Final Office Action received in U.S. Appl. No. 14/760,465 dated May 3, 2016.
International Search Report and Written Opinion received in International Application No. PCT/US2014/064436, dated Nov. 20, 2014.
Final Office Action received in U.S. Appl. No. 14/760,465 dated Sep. 7, 2016.
International Search Report and Written Opinion received in International Application No. PCT/EP2013/050468, dated Oct. 29, 2013.
Non-Final Office Action received in U.S. Appl. No. 15/319,734 dated Feb. 28, 2018.

* cited by examiner

600

| Time Increment | Control Parameter Value |
|---|---|
| 0 hrs | 1000 microamps |
| 12 hrs | 1010 microamps |
| 24 hrs | 1020 microamps |
| 36 hrs | 1030 microamps |
| 48 hrs | 1040 microamps |
| 60 hrs | 1050 microamps |
| 72 hrs | 1060 microamps |
| 84 hrs | 1070 microamps |
| 96 hrs | 1080 microamps |

SYSTEMS AND METHODS FOR GRADUALLY ADJUSTING A CONTROL PARAMETER ASSOCIATED WITH A COCHLEAR IMPLANT SYSTEM

BACKGROUND INFORMATION

When a cochlear implant of a cochlear implant system is initially implanted in a patient, and during follow-up tests and checkups thereafter, it is usually necessary to fit the cochlear implant system to the patient. For example, during a fitting session, a clinician may utilize a fitting system to set various control parameters associated with (e.g., that govern an operation of) the cochlear implant system and/or otherwise configure the cochlear implant system for operation.

One of the control parameters that is often set during a fitting session for a cochlear implant patient is a most comfortable level ("M level"). An M level represents a stimulation current level required to achieve comfortable loudness to the patient. In other words, the M level represents a stimulation current level, which, when applied to a given set of one or more electrodes associated with the M level, produces a sensed perception of sound by the patient that is moderately loud, or comfortably loud, but not so loud that the perceived sound is uncomfortable.

An M level is typically determined by sequentially increasing the stimulation current level for the patient until the patient reports a comfortably loud sound on a subjective loudness scale. Because the M level anchors the patient's mapping function, defines the patient's electrical dynamic range (thereby impacting a host of perceptual attributes, such as loudness, sound-field-thresholds, spectral contrast, etc.), and is often used to derive other control parameters, accurately determining the M level is highly desirable.

It is a common observation that M levels are often under-fit (i.e., set to be lower than what the patient can actually tolerate) during the fitting process. This is at least in part due to the fact that the patient's tolerance of electrical stimulation is strongly influenced by sound exposure. Many cochlear implant patients have not had much, if any, exposure to loud sounds prior to being implanted with a cochlear implant. Hence, these patients may not initially be able to tolerate relatively high M levels, even though their ability to tolerate high M levels may increase over time as they are exposed to more loud sounds.

Unfortunately, however, M levels are only adjusted during fitting sessions (i.e., when the patient visits a clinic). This means that the M levels are held constant in between the fitting sessions, even though the ability of a patient to tolerate different electrical stimulation levels may fluctuate over time as the patient is exposed to different levels of sound.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
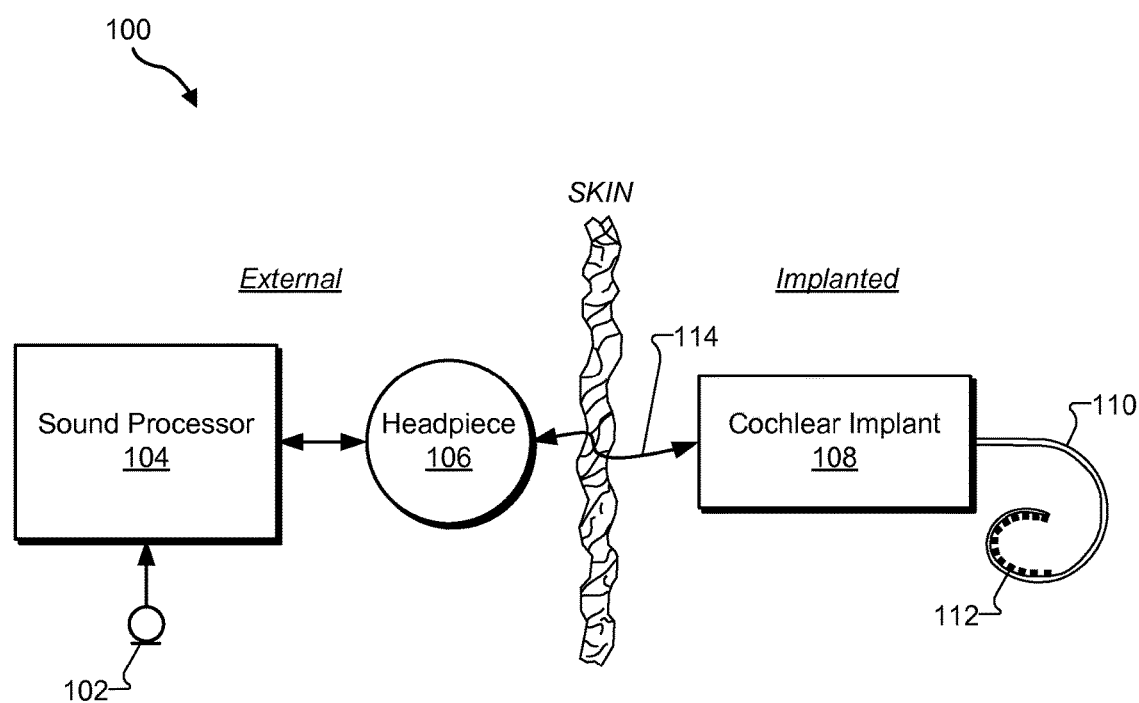
FIG. 1 illustrates an exemplary cochlear implant system according to principles described herein.

Systems and methods for gradually adjusting a control parameter associated with a cochlear implant system are described herein. As will be described below, a sound processor included in a cochlear implant system associated with a patient may receive, from a fitting system while the sound processor is communicatively coupled to the fitting system, a command that sets a control parameter associated with the cochlear implant system to an initial value and data representative of a target value associated with the control parameter. The sound processor may subsequently enter a non-fitting state by being decoupled from the fitting system. While in the non-fitting state, the sound processor may gradually adjust the control parameter from the initial value towards the target value in accordance with an adaption time course associated with the control parameter.

As an example, a fitting system may be used by a clinician to initially fit a cochlear implant system to a patient subsequent to the patient being implanted with a cochlear implant. To this end, the clinician may connect a sound processor included in the cochlear implant system to the fitting system (e.g., by way of a clinician's programming interface ("CPI") device). While the sound processor is connected to the fitting system, the clinician may perform one or more procedures to determine an initial value for an M level associated with the patient. As mentioned, this initial value for the M level may be under-fit (i.e., less than a target value for the M level that the patient should subsequently be able to tolerate after being exposed to sound over the course of a certain amount of time). To facilitate patient adaption to the target value of the M level, the clinician may use the fitting system to transmit, to the sound processor, a command that sets the M level to the initial value, data representative of a target value associated with the M level, and data representative of an adaption time course associated with the M level. As will be illustrated below, the adaption time course may specify a time course during which the M level is to be gradually adjusted by the sound processor from the initial value towards the target value.

After the fitting session is over, the sound processor may be decoupled from the fitting system (e.g., by being disconnected from the CPI device). The sound processor may detect this decoupling and, in response, enter a non-fitting state in which the sound processor may operate normally (e.g., by locking to the cochlear implant and, while locked, directing the cochlear implant to apply electrical stimulation representative of audio signals received and processed by the sound processor).

While in the non-fitting state, the sound processor may gradually adjust the M level from the initial value towards the target value in accordance with the adaption time course associated with the M level. For example, the sound processor may adjust the M level such that the M level trends upward towards the target value. As will be described below, incremental increases and decreases in the M level may occur during the trending upward towards the target value based on one or more other time-based and environmental-based factors.

The gradual adjustment of the M level may cease once the M level has reached the target level. Additionally or alternatively, the gradual adjustment of the M level may cease in response to user input provided by the patient.

By gradually adjusting a control parameter associated with a cochlear implant in this manner, the systems and methods described herein may facilitate patient adaption to a target value for the control parameter without requiring the patient to attend multiple fitting sessions. This may save the patient (and the clinician) time and resources. Moreover, the gradual adjustment of a control parameter as described herein may optimize cochlear implant system performance and allow for more accurate sound representation to the patient. Other benefits of the present systems and methods will be made apparent herein.

As used herein, a "control parameter" associated with a cochlear implant system may refer to any setting, stimulation parameter, and/or other parameter that governs an operation of one or more components included in the cochlear implant system. For example, a control parameter may be an M level, a threshold level ("T level"), an input dynamic range ("IDR"), a stimulation rate, and/or a pulse width. As described above, an M level represents a stimulation current level required to achieve comfortable loudness to the patient. A T level represents a minimum stimulation current level that produces a sensed perception of sound by the patient. IDR represents the difference (in SPL) between a sound amplitude producing T level stimulation and a sound amplitude producing M level stimulation. Stimulation rate refers to how many stimulation pulses per second may be applied by way of a given set of one or more electrodes. Pulse width refers to a width of each stimulation pulse that is applied by way of the given set of one or more electrodes.

Each of the control parameters described herein may be stimulation channel-specific. As used herein, a "stimulation channel" refers to a set of one or more electrodes by way of which electrical stimulation may be applied to a stimulation site within a cochlear implant patient. Because there may be multiple stimulation channels within a cochlear implant system, there may be multiple instances of a particular control parameter. For example, there may be a plurality of M levels each associated with a different stimulation channel. Alternatively, a single instance of a control parameter may be associated with all of the stimulation channels within a cochlear implant system.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an intracochlear electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
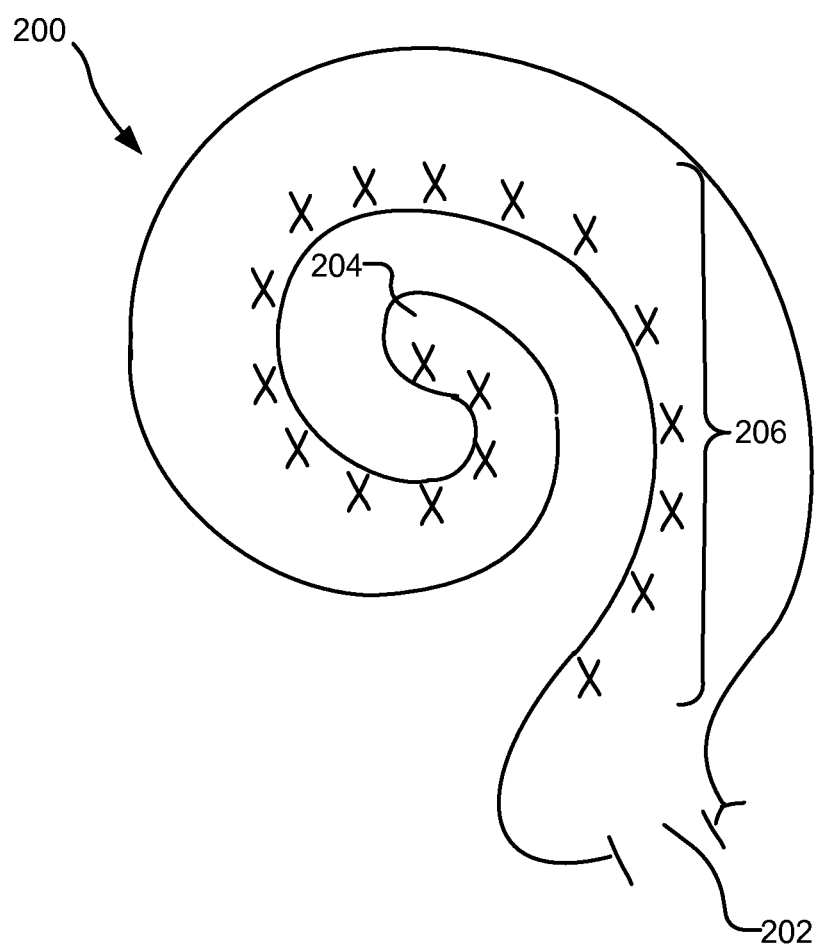
FIG. 2 illustrates a schematic structure of the human cochlea according to principles described herein.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
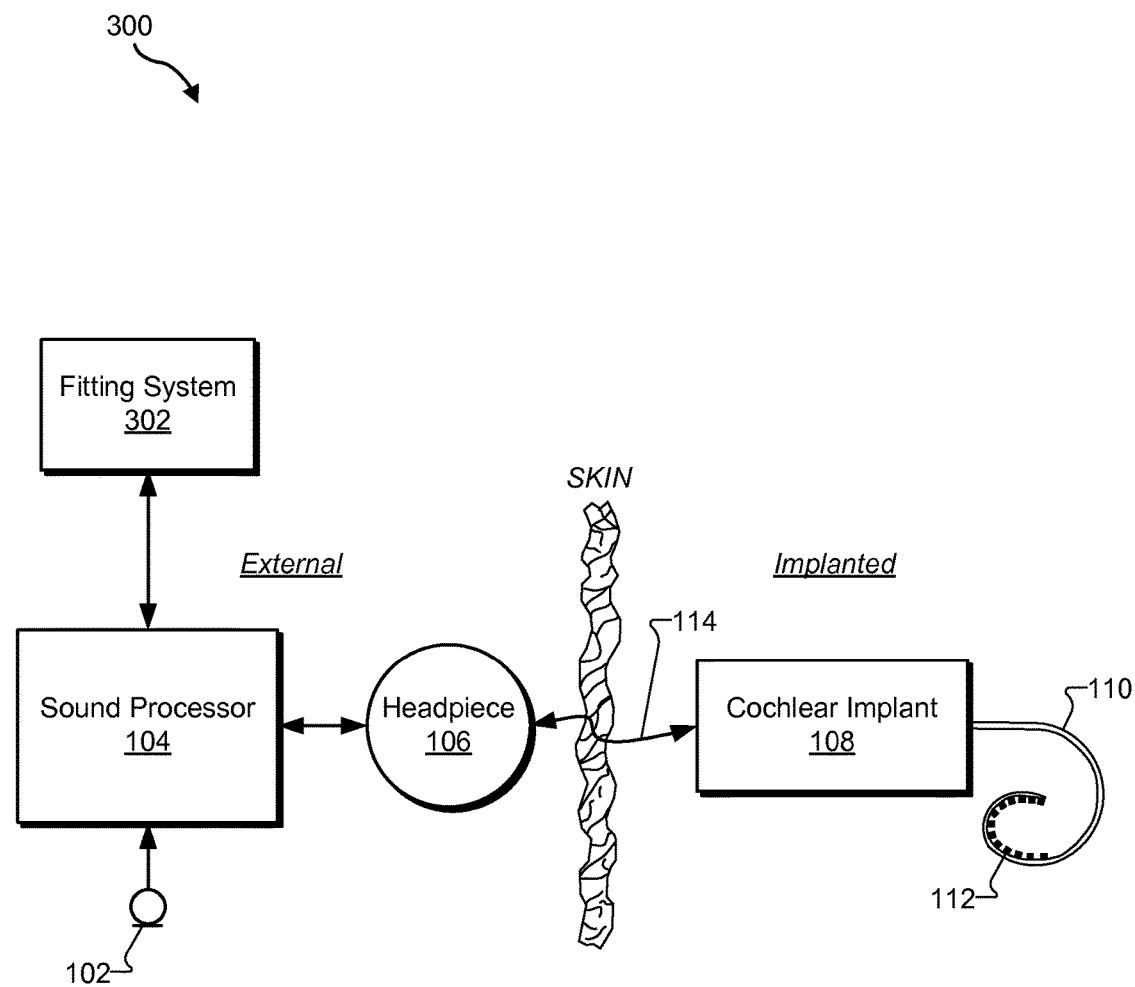
FIG. 3 shows an exemplary configuration in which a fitting system is communicatively coupled to the cochlear implant system shown in FIG. 1 according to principles described herein.

FIG. 3 shows an exemplary configuration 300 in which a fitting system 302 is communicatively coupled to cochlear implant system 100 by way of sound processor 104. Fitting system 302 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component or computing device as may serve a particular implementation. In some examples, fitting system 302 may provide one or more graphical user interfaces ("GUIs") (e.g., by presenting the one or more GUIs by way of a display screen) with which a clinician or other user may interact.

Fitting system 302 may be selectively coupled to sound processor 104 in any suitable manner. While coupled to sound processor 104, fitting system 302 may be used to perform various types of fitting procedures with respect to cochlear implant system 100. For example, fitting system 302 may program sound processor 104 to operate in accordance with one or more sound processing programs, adjust one or more control parameters associated with cochlear implant system 100 (e.g., by transmitting a command to sound processor 104 that sets a particular control parameter to a particular value), and/or perform any other suitable operation with respect to cochlear implant system 100.

Figure 4:
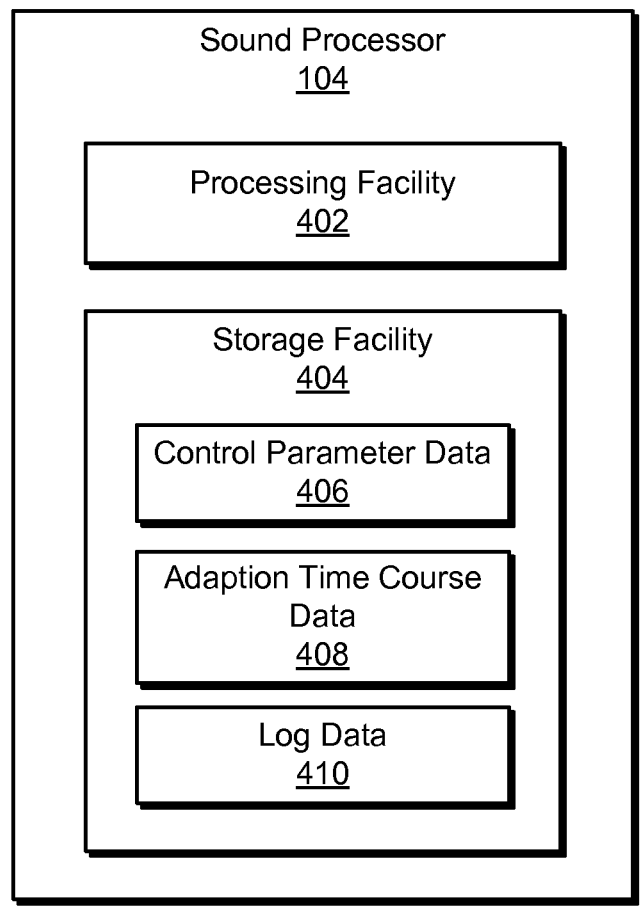
FIG. 4 illustrates exemplary components of a sound processor according to principles described herein.

FIG. 4 illustrates exemplary components of sound processor 104. It will be recognized that the components shown in FIG. 4 are merely representative of the many different components that may be included in sound processor 104 and that sound processor 104 may include additional or alternative components as may serve a particular implementation.

As shown in FIG. 4, sound processor 104 may include a processing facility 402 and a storage facility 404, which may be in communication with one another using any suitable communication technologies. Processing facility 402 and/or storage facility 404 may include or be implemented by a computing device or processor configured to perform one or more of the functions described herein.

Storage facility 404 may maintain control parameter data 406, adaption time course data 408, and log data 410 received, generated, and/or used by processing facility 402. Control parameter data 406 may include, but is not limited to, an initial value of a control parameter, a target value of the control parameter, and/or any other data associated with the control parameter. Adaption time course data 408 may include data representative of an adaption time course associated with a particular control parameter. Log data 410 may include data representative of a history of a gradual adjustment of a control parameter. Storage facility 404 may maintain additional or alternative data as may serve a particular implementation.

Processing facility 402 may perform various operations with respect to cochlear implant system 100 and/or fitting system 302. For example, processing facility 402 may process an audio signal detected by microphone 102, and, based on the processing, direct cochlear implant 108 to generate and apply electrical stimulation representative of the audio signal to one or more stimulation sites within the patient by way of one or more electrodes 112. As another example, processing facility 402 may detect a coupling of sound processor 104 to fitting system 302, and, in response, direct sound processor 104 to enter a "fitting state" in order to facilitate programming of sound processor 104 by fitting system 302. Processing facility 402 may subsequently detect a decoupling of sound processor 104 from fitting system 302, and, in response, direct sound processor to enter a "non-fitting state" in which sound processor 104 may operate normally. Various specific operations of processing facility 402 associated with gradually adjusting a control parameter will now be described.

As mentioned, it may be desirable to gradually and automatically adjust a control parameter associated with cochlear implant system 100 in between fitting sessions. For example, a cochlear implant patient may be initially able to tolerate a relatively low M level during a fitting session and shortly thereafter. However, after being exposed to sounds for an extended period of time (e.g., days or weeks), the patient may be able to tolerate a relatively higher M level. Hence, it may be desirable to dynamically increase the M level for the patient as the patient becomes more accustomed to sound without requiring the patient to participate in repeated fitting sessions (which would typically require the patient to make multiple trips to the clinic).

To this end, during a fitting session in which sound processor 104 is communicatively coupled to fitting system 302, a clinician and/or the fitting system 302 itself may determine an initial value and a target value for a control parameter. The initial value may be determined in any suitable manner (e.g., in accordance with subjective feedback from the patient). Likewise, the target value may be determined in any suitable manner (e.g., by eliciting and measuring a stapedius reflex ("eSRT") and/or any other objective measure, setting the target value to automatically be a predetermined percentage (e.g., twenty percent) higher than the initial value, and or in any other manner). The target value may be greater than or less than the initial value depending on the particular control parameter. For example, if the control parameter is an M level, the target value may be greater than the initial value. Alternatively, if the control parameter is pulse width, the target value may be less than the initial value.

Fitting system 302 may transmit a command to sound processor 104 that sets the control parameter to the initial value. Fitting system 302 may also transmit data representative of the target value to sound processor 104. Processing facility 402 may receive the command that sets the control parameter to the initial value and the data representative of the target value in any suitable manner.

In some examples, the clinician and/or the fitting system 302 itself may also specify an adaption time course associated with the control parameter. Fitting system 302 may transmit data representative of the adaption time course to sound processor 104. Processing facility 402 may receive the data representative of the adaption time course and store this data within storage facility 404 (e.g., in the form of adaption time course data 408). Alternatively, sound processor 104 may be pre-programmed with data representative of the adaption time course.

Figure 5:
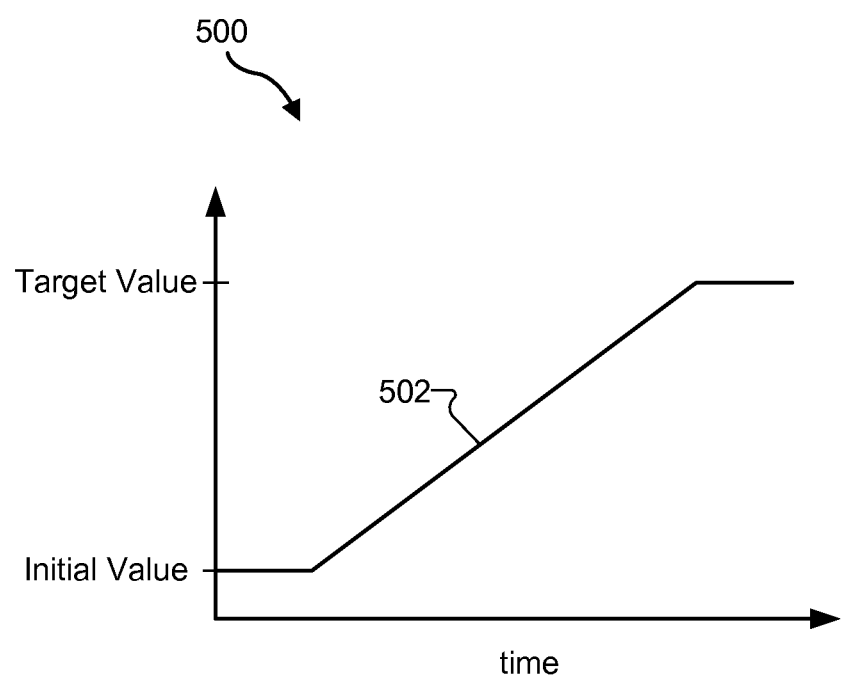
FIG. 5 shows a graphical representation of an adaption time course for a control parameter according to principles described herein.

The adaption time adaption time course may specify a time course during which the control parameter is to be gradually adjusted by sound processor 104 from the initial value towards the target value. To illustrate, FIG. 5 shows a graphical representation 500 of an adaption time course for a control parameter. In graphical representation 500, line 502 represents the value of a particular control parameter as a function of time. As shown, as time progresses, the value of the control parameter gradually increases from an initial value towards a target value. In the particular example of FIG. 5, the gradual increase is linear. However, it will be recognized that other adaption time courses may specify that the control parameter increases and/or decreases in any other manner (e.g., the rate of increase for the control parameter may increase as time progresses).

Figure 6:
FIG. 6 shows an exemplary look-up table that includes data representative of an adaption time course for a particular control parameter according to principles described herein.

Data representative of the adaption time course may be received and maintained by sound processor 104 in any suitable manner. For example, data representative of the adaption time course may be maintained by sound processor 104 in the form of a look-up table. To illustrate, FIG. 6 shows an exemplary look-up table 600 that includes data representative of an adaption time course for a particular control parameter (e.g., an M level) and that may be maintained by sound processor 104.

As shown, look-up table 600 specifies a plurality of time increments and a series of control parameter values. Each time increment represents an amount of elapsed time with respect to a start time (which may correspond to a time that the sound processor 104 is decoupled from fitting system 302, a time that the sound processor 104 first locks to a cochlear implant subsequent to being decoupled from fitting system 302, and/or a time associated with any other event as may serve a particular implementation).

Each control parameter value included in look-up table 600 represents a value that the control parameter is to be set to at each time increment. For example, look-up table 600 indicates that the control parameter is to be set by processing facility 402 to 1000 microamps at a time increment of zero hours (i.e., 1000 microamps is the initial value). After 12 hours have elapsed, the control parameter is to be increased by processing facility 402 to 1010 microamps. Likewise, after 24 hours have elapsed, the control parameter is to be increased by processing facility 402 to 1020 microamps. The control parameter may be gradually increased by processing facility 402 in this manner until the control parameter maxes out at the target value (which, in this example, is 1080 microamps and occurs at a time interval of 96 hours). By gradually increasing the control parameter in this manner, processing facility 402 may allow the patient to adapt to each increased value without even noticing that the control parameter is being adjusted.

Once the command to set the control parameter to the initial value and the data representative of the target value are transmitted to sound processor 104 during a fitting session, sound processor 104 may be decoupled from fitting system 302. Processing facility 402 may detect this decoupling in any suitable manner. In response to the decoupling, processing facility 402 may direct sound processor 104 to enter a non-fitting state. While the sound processor 104 is in the non-fitting state, processing facility 402 may gradually adjust the control parameter from the initial value towards the target value in accordance with the adaption time course associated with the control parameter. This may be performed in any suitable manner.

For example, processing facility 402 may adjust the control parameter in accordance with the data included in look-up table 600. To this end, processing facility 402 may track an elapsing of time (e.g., beginning with the decoupling of sound processor 104 from fitting system 302) and incrementally adjust the control parameter to a next value included in the series of values in response to an occurrence, within the elapsing of time, of each time increment included in the plurality of time increments. For example, in response to an elapsing of 12 hours, processing facility 402 may adjust the control parameter from 1000 microamps to 1010 microamps. This process may continue until the control parameter maxes out at the target value.

Processing facility 402 may track the elapsing of time in any suitable manner. For example, processing facility 402 may track the elapsing of time by tracking a total number of clock cycles that elapse subsequent to a starting event (e.g., an initial locking of sound processor 104 to cochlear implant 108). Additionally or alternatively, processing facility 402 may utilize a clock that tracks time in terms of any other suitable increment (e.g., seconds, minutes, hours, and/or days).

In some examples, processing facility 402 may adjust the control parameter while sound processor 104 is locked to cochlear implant 108 and abstain from adjusting the control parameter 104 while sound processor 104 is not locked to cochlear implant 108. As used herein, the sound processor 104 may be "locked" to cochlear implant 108 while sound processor 104 is actively communicating with cochlear implant 108. For example, sound processor 104 may lock to cochlear implant 108 each morning when the patient turns "on" sound processor 104, but may not be locked to cochlear implant 108 after the patient turns the sound processor 104

"off" (e.g., at night while the patient sleeps). Processing facility 402 may detect that sound processor 104 is or is not locked to cochlear implant 108 in any suitable manner.

In cases where processing facility 402 only adjusts the control parameter while sound processor 104 is locked to cochlear implant 108, the adaption time course may not take into account time periods during which sound processor 104 is not locked to cochlear implant 108. In other words, the time intervals shown in look-up table 600 may only be tracked while sound processor 104 is locked to cochlear implant 108. In some alternative embodiments, the adaption time course does take into account time periods during which sound processor 104 is not locked to cochlear implant 108. In these alternative embodiments, the time intervals shown in look-up table 600 are tracked regardless of whether sound processor 104 is locked to cochlear implant 108.

In some examples, processing facility 402 may adjust the control parameter until the control parameter reaches the target value. Processing facility 402 may detect that the control parameter has reached the target value and, in response, cease the adjustment of the control parameter. At any point before the control parameter reaches the target value, the patient may provide user input (e.g., by pressing a button on the sound processor 104) representative of a command to cease adjusting the control parameter. Processing facility 402 may detect this user input and, in response, cease the adjustment of the control parameter. Such user input may be provided, for example, if the user experiences pain and/or discomfort as a result of the gradual adjustment of the control parameter.

Processing facility 402 may take into account one or more other time-based and/or environmental-based factors while gradually adjusting the control parameter towards the target value. For example, processing facility 402 may take into account a time of day while gradually adjusting the M level (or any other control parameter) towards the target value. This is because electrical stimulation experienced by the patient early in the morning after a night of device deactivation is most likely perceived as being very loud compared to the same stimulation received later in the day when the patient has had more substantial exposure to sound. This is akin to a stereo sounding uncomfortably loud when it is turned on in the morning from a state that it was in during a loud party the previous night.

Figure 7:
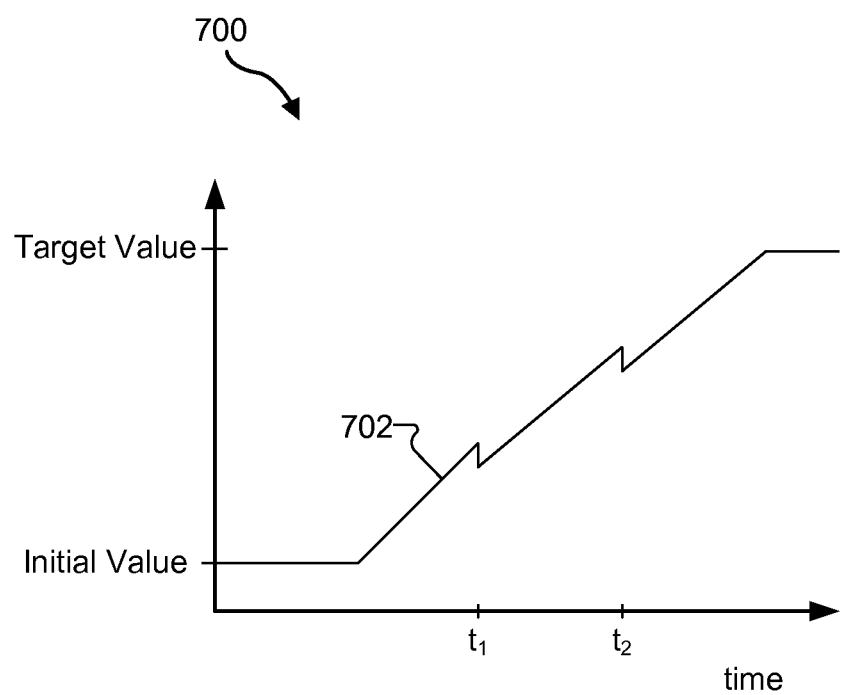
FIG. 7 shows a graphical representation of an adaption time course for a control parameter according to principles described herein.

Hence, processing facility 402 may incrementally decrease the M level each morning when sound processor 104 locks to cochlear implant 108 so that sounds do not appear to be overly loud to the patient. Processing facility 402 may then increase the M level as the time of day progresses in accordance with the adaption time course. This is illustrated in FIG. 7, which shows a graphical representation 700 of an adaption time course that has been modified to take into account the time of day. Line 702 represents the value of a particular M level as a function of time. As shown, as time progresses, the value of the M level gradually trends upwards from an initial value towards a target value. However, FIG. 7 shows that at times $t_1$ and $t_2$, which correspond to times in the mornings of subsequent days when the sound processor 104 first locks to the cochlear implant 108, processing facility 402 incrementally decreases the M level.

As mentioned, processing facility 402 may additionally or alternatively take into account one or more other environmental-based factors while gradually adjusting the control parameter towards the target value. For example, processing facility 402 may take into account an amount of sound exposure to the patient during a determined time period while gradually adjusting the M level (or any other control parameter) towards the target value.

For example, processing facility 402 may detect an amount of sound exposure to the patient within a predetermined time period and perform the gradual adjustment of the control parameter from the initial value towards the target value in accordance with the detected amount of sound exposure to the patient within the predetermined time period. The predetermined time period may be any suitable amount of time as may serve a particular implementation. For example, the predetermined time period may be relatively short when taking into account instantaneous sound exposure to the patient. Alternatively, the predetermined time period may be relatively long when taking into account average sound exposure to the patient.

Processing facility 402 may detect the amount of sound exposure to the patient in any suitable manner. For example, processing facility 402 may detect the amount of sound exposure to the patient by detecting a sound level (e.g., an amplitude) of an audio signal received by microphone 102 and average the sound level over the predetermined time period.

In some examples, if the detected amount of sound exposure is above a first threshold within the predetermined time period, processing facility 402 may increase the control parameter (e.g., by an incremental amount). Similarly, if the detected amount of sound exposure is below a second threshold (which may be the same as or less than the first threshold) within the predetermined time period, processing facility 402 may decrease the control parameter (e.g., by an incremental amount).

For example, if the patient enters and stays in an environment that has relatively loud sounds (e.g., a noisy restaurant), processing facility 402 may at least temporarily increase an M level associated with the patient. In some examples, the M level (or any other control parameter) may be temporarily adjusted (e.g., increased) only after the patient has been in the relatively loud environment for a predetermined amount of time (e.g., a few hours, a day, etc.). This would ensure that the patient has had sufficient exposure to the current value of the M level before further adjusting the M level. When the patient leaves the loud environment and enters a relatively quiet environment (e.g., the patient's home), processing facility 402 may decrease the M level associated with the patient (e.g., after a predetermined amount of time). It will be recognized that these incremental increases and decreases in response to changing sound exposure may be performed on top of (i.e., in addition to) the underlying gradual adjustment of the control parameter in accordance with the adaption time course.

In some examples, processing facility 402 may log a history of the gradual adjustment of the control parameter. Processing facility 402 may then detect a coupling of sound processor 104 to fitting system 302 subsequent to logging the history, and, in response, transmit data representative of the logged history to fitting system 302. A clinician may then utilize fitting system 302 to perform one or more analysis operations with respect to the logged history in order to further optimize the control parameter.

In some examples, a cochlear implant system may include a bilateral configuration wherein separate cochlear implants are implanted for both ears of the patient. In this configuration, the patient may utilize a first sound processor for the first ear and a second sound processor for the second ear. In some examples, control parameters associated with each sound processor may be gradually adjusted in accordance with the systems and methods described herein. The sound processors may coordinate the adjustment of the control parameters (e.g., by way of a wireless link between the sound processors.

In some alternative examples, a cochlear implant system may be included in a bimodal configuration wherein the patient is fitted with a cochlear implant for his/her first ear and a hearing aid for his/her second ear. In this configuration, control parameters associated with both the cochlear implant system and the hearing aid may be gradually adjusted in accordance with the systems and methods described herein. The adjustment may be coordinated in any suitable manner.

Figure 8:
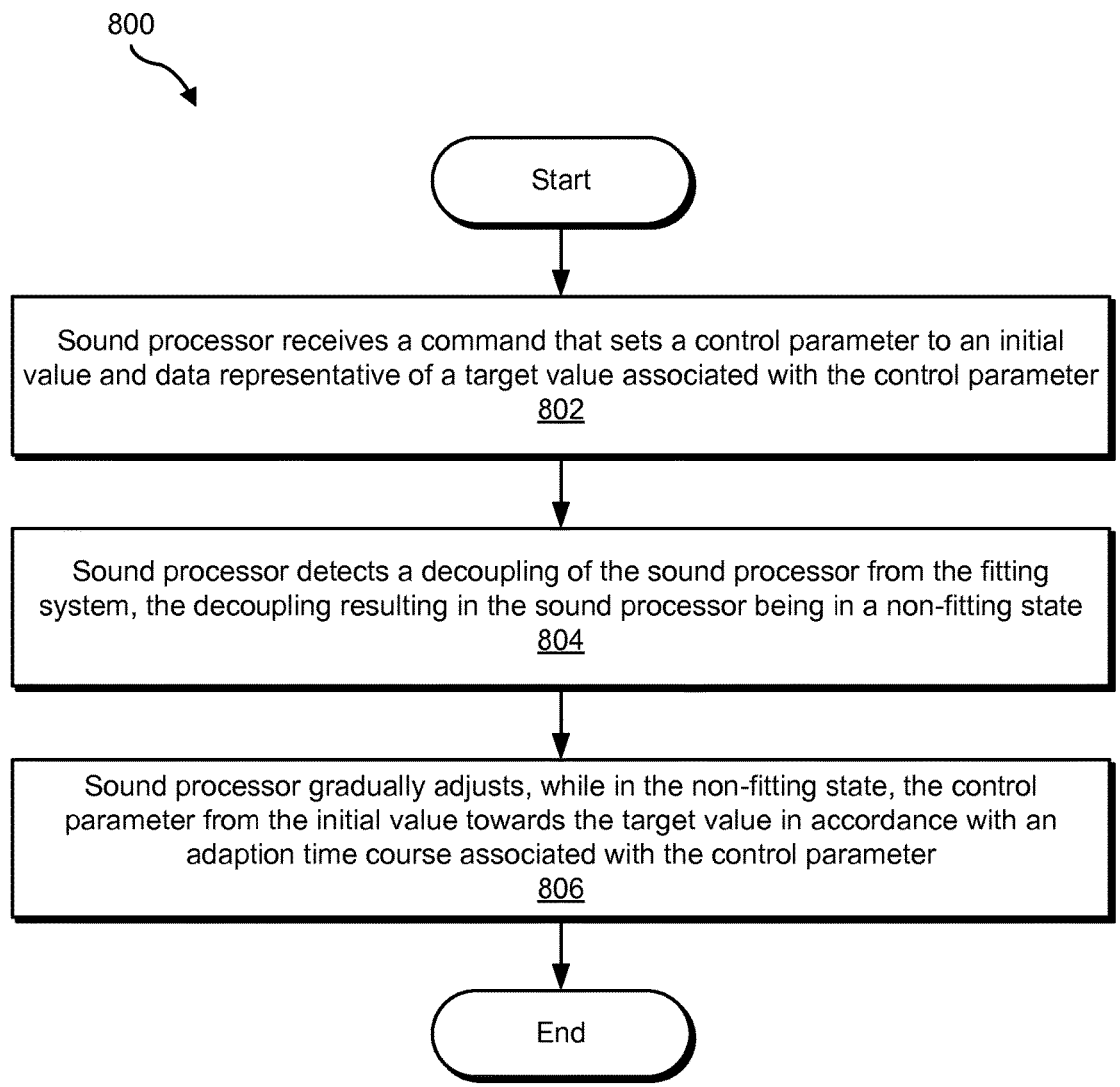
FIG. 8 illustrates an exemplary method of gradually adjusting a control parameter associated with a cochlear implant system.

FIG. 8 illustrates an exemplary method 800 of gradually adjusting a control parameter associated with a cochlear implant system. While FIG. 8 illustrates exemplary steps according to one embodiment, other embodiments may omit, add to, reorder, and/or modify any of the steps shown in FIG. 8. One or more of the steps shown in FIG. 8 may be performed by sound processor 104 and/or any implementation thereof.

In step 802, a sound processor receives a command that sets a control parameter to an initial value and data representative of a target value associated with the control parameter. The sound processor may receive the command and data from a fitting system while the sound processor is communicatively coupled to the fitting system. Step 802 may be performed in any of the ways described herein.

In step 804, the sound processor detects a decoupling of the sound processor from the fitting system, the decoupling resulting in the sound processor being in a non-fitting state. Step 804 may be performed in any of the ways described herein.

In step 806, the sound processor gradually adjusts, while in the non-fitting state, the control parameter from the initial value towards the target value in accordance with an adaption time course associated with the control parameter. Step 806 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A cochlear implant system comprising:
 a cochlear implant configured to be implanted within a patient; and
 a sound processor configured to
  receive, from a fitting system during a fitting session,
   a command that sets a most comfortable level ("M level") to an initial value, the initial value of the M level representing a first stimulation current level required for the cochlear implant to produce a sensed perception of sound that is comfortably loud for the patient during the fitting session, and
   a target value for the M level, the target value for the M level representing a second stimulation current level that is greater than the first stimulation current level and that is required for the cochlear implant to produce a sensed perception of sound that is comfortably loud for the patient at a time subsequent to the fitting session;
  store an adaption time course that specifies a plurality of time increments and a series of values between the initial value and the target value;
  detect a decoupling of the sound processor from the fitting system, the decoupling resulting in the sound processor being in a non-fitting state;
  gradually adjust, while the sound processor is in the non-fitting state and subsequent to the fitting session, the M level from the initial value towards the target value in accordance with the adaption time course; and
  direct the cochlear implant to apply stimulation having the gradually adjusted M level to the patient;
 wherein the sound processor is configured to gradually adjust the M level from the initial value towards the target value by:
  tracking an elapsing of time beginning with the decoupling of the sound processor from the fitting system; and
  incrementally adjusting the M level to a next different value included in the series of values in response to an occurrence, within the elapsing of time, of each time increment included in the plurality of time increments.

2. The cochlear implant system of claim 1, wherein the sound processor is configured to receive data representative of the adaption time course associated from the fitting system while the sound processor is communicatively coupled to the fitting system.

3. The cochlear implant system of claim 1, wherein the sound processor is further configured to:
 gradually adjust the M level from the initial value towards the target value by detecting when the sound processor is locked to the cochlear implant and adjusting the M level while the sound processor is locked to the cochlear implant; and
 abstain from adjusting the M level while the sound processor is not locked to the cochlear implant.

4. The cochlear implant system of claim 1, wherein the sound processor is further configured to:
 detect that the M level has reached the target value; and
 cease, in response to the M level reaching the target value, the adjustment of the M level.

5. The cochlear implant system of claim 1, wherein the sound processor is further configured to:
 detect user input representative of a command to cease adjusting the M level before the M level reaches the target value; and
 cease, in response to the user input, the adjustment of the M level.

6. The cochlear implant system of claim 1, wherein the gradual adjustment of the M level from the initial value towards the target value is further performed by the sound processor in accordance with a time of day.

7. The sound processor of claim 6, wherein the processing facility gradually adjusts the M level in accordance with the time of day by
 incrementally decreasing the M level when the sound processor first locks to a cochlear implant during the day; and
 increasing the M level as the time of day progresses.

8. The cochlear implant system of claim 1, wherein the sound processor is further configured to:
 detect an amount of sound exposure to the patient within a predetermined time period; and
 further perform the gradual adjustment of the M level from the initial value towards the target value in accordance with the detected amount of sound exposure to the patient within the predetermined time period.

9. The cochlear implant system of claim 8, wherein the sound processor is further configured to:
increase the M level if the detected amount of sound exposure is above a first threshold within the predetermined time period; and
decrease the M level if the detected amount of sound exposure is below a second threshold within the predetermined time period.

10. The cochlear implant system of claim 1, wherein the sound processor is further configured to:
receive, from the fitting system during the fitting session, a command that sets an additional control parameter other than the M level to an additional initial value, and
data representative of an additional target value; and
gradually adjust, while the sound processor is in the non-fitting state and subsequent to the fitting session, the additional control parameter from the additional initial value towards the additional target value in accordance with an additional adaption time;
wherein the additional control parameter comprises at least one of a threshold level ("T level"), an input dynamic range ("IDR"), a stimulation rate, and a pulse width.

11. The cochlear implant system of claim 1, wherein the sound processor is further configured to log a history of the gradual adjustment of the M level.

12. The cochlear implant system of claim 11, wherein the sound processor is further configured to:
detect a communicative coupling of the sound processor to the fitting system subsequent to the gradual adjustment of the M level; and
transmit, while the sound processor is communicatively coupled to the fitting system subsequent to the gradual adjustment of the M level, data representative of the logged history to the fitting system.

13. A system comprising:
a cochlear implant configured to be implanted within a patient; and
a sound processor configured to control the cochlear implant; and
a fitting system configured to
transmit, during a fitting session,
a command that sets a most comfortable level ("M level") to an initial value, the initial value of the M level representing a first stimulation current level required for the cochlear implant to produce a sensed perception of sound that is comfortably loud for the patient during the fitting session,
a target value for the M level, the target value for the M level representing a second stimulation current level that is greater than the first stimulation current level and that is required for the cochlear implant to produce a sensed perception of sound that is comfortably loud for the patient at a time subsequent to the fitting session, and
an adaption time course that specifies a plurality of time increments and a series of values between the initial value and the target value;
wherein the sound processor is configured to
receive the command, the target value, and the adaption time course from the fitting system,
detect a decoupling of the sound processor from the fitting system,
gradually adjust, subsequent to being decoupled from the fitting system and subsequent to the fitting session, the M level from the initial value towards the target value in accordance with the adaption time, and
direct the cochlear implant to apply stimulation having the gradually adjusted M level to the patient;
wherein the sound processor is configured to gradually adjust the M level from the initial value towards the target value by:
tracking an elapsing of time beginning with the decoupling of the sound processor from the fitting system; and
incrementally adjusting the M level to a next different value included in the series of values in response to an occurrence, within the elapsing of time, of each time increment included in the plurality of time increments.

14. The system of claim 13, wherein:
the sound processor is further configured to
log a history of the gradual adjustment of the M level, and
transmit, while the sound processor is again communicatively coupled to the fitting system subsequent to the gradual adjustment of the M level, data representative of the logged history; and
the fitting system is further configured to
receive the data representative of the logged history, and
perform one or more analysis actions with respect to the logged history.

15. A method comprising:
receiving, by a sound processor during a fitting session with a fitting system,
a command that sets a most comfortable level ("M level") to an initial value, the initial value of the M level representing a first stimulation current level required for a cochlear implant to produce a sensed perception of sound that is comfortably loud for the patient during the fitting session, and
a target value for the M level, the target value of the M level representing a second stimulation current level that is greater than the first stimulation current level and that is required for the cochlear implant to produce a sensed perception of sound that is comfortably loud for the patient at a time subsequent to the fitting session;
storing, by the sound processor, an adaption time course that specifies a plurality of time increments and a series of values between the initial value and the target value;
detecting, by the sound processor, a decoupling of the sound processor from the fitting system, the decoupling resulting in the sound processor being in a non-fitting state;
gradually adjusting, by the sound processor while the sound processor is in the non-fitting state and subsequent to the fitting session, the M level from the initial value towards the target value in accordance with the adaption time course; and
directing the cochlear implant to apply stimulation having the gradually adjusted M level to the patient;
wherein the gradual adjusting comprises:
tracking an elapsing of time beginning with the decoupling of the sound processor from the fitting system; and
incrementally adjusting the M level to a next different value included in the series of values in response to an occurrence, within the elapsing of time, of each time increment included in the plurality of time increments.

16. The method of claim 15, further comprising receiving data representative of the adaption time course from the fitting system while the sound processor is communicatively coupled to the fitting system.

17. The method of claim 15, further comprising:
receiving, by the sound processor during the fitting session,
  a command that sets an additional control parameter other than the M level to an additional initial value, and
  data representative of an additional target value; and
gradually adjusting, by the sound processor while the sound processor is in the non-fitting state and subsequent to the fitting session, the additional control parameter from the additional initial value towards the additional target value in accordance with an additional adaption time course;
wherein the additional control parameter comprises at least one of a threshold level ("T level"), an input dynamic range ("IDR"), a stimulation rate, and a pulse width.

\* \* \* \* \*